US009061003B2

(12) United States Patent
Sugihara et al.

(10) Patent No.: US 9,061,003 B2
(45) Date of Patent: Jun. 23, 2015

(54) THERAPEUTIC OR PREVENTIVE AGENT FOR DIABETES

(75) Inventors: Fumihito Sugihara, Yao (JP); Naoki Inoue, Yao (JP); Seiko Koizumi, Yao (JP); Tadashi Yoshimoto, Nara (JP); Hiroshi Oyama, Hirakata (JP)

(73) Assignee: NITTA GELATIN INC., Osaka (JP)

( * ) Notice: Subject to any disclaimer, the term of this patent is extended or adjusted under 35 U.S.C. 154(b) by 0 days.

(21) Appl. No.: 13/981,258

(22) PCT Filed: Jan. 25, 2012

(86) PCT No.: PCT/JP2012/051561
§ 371 (c)(1),
(2), (4) Date: Jul. 23, 2013

(87) PCT Pub. No.: WO2012/102308
PCT Pub. Date: Aug. 2, 2012

(65) Prior Publication Data
US 2013/0303448 A1    Nov. 14, 2013

(30) Foreign Application Priority Data

Jan. 27, 2011    (JP) .................................. 2011-015095

(51) Int. Cl.
| A61K 38/39 | (2006.01) |
| A61K 38/05 | (2006.01) |
| A61K 38/06 | (2006.01) |
| C07K 5/062 | (2006.01) |
| C07K 5/065 | (2006.01) |
| C07K 5/072 | (2006.01) |
| C07K 5/083 | (2006.01) |
| C07K 5/087 | (2006.01) |
| C07K 5/093 | (2006.01) |
| C07K 5/097 | (2006.01) |

(52) U.S. Cl.
CPC ................. *A61K 38/39* (2013.01); *A61K 38/05* (2013.01); *A61K 38/06* (2013.01); *C07K 5/06043* (2013.01); *C07K 5/0606* (2013.01); *C07K 5/06078* (2013.01); *C07K 5/06104* (2013.01); *C07K 5/0806* (2013.01); *C07K 5/0812* (2013.01); *C07K 5/0819* (2013.01); *C07K 5/0823* (2013.01)

(58) Field of Classification Search
None
See application file for complete search history.

(56) References Cited

U.S. PATENT DOCUMENTS

2008/0221023 A1* 9/2008 Boots ............................ 514/12

FOREIGN PATENT DOCUMENTS

| JP | 2002-326951 | 11/2002 |
| JP | 2002326951 A | 11/2002 |
| JP | 2007-039424 | 2/2007 |
| JP | 2009-284798 | 12/2009 |
| JP | 2010-013423 | 1/2010 |
| JP | 2010-138143 | 6/2010 |
| WO | 2008/066070 | 6/2008 |
| WO | 2009/035169 | 3/2009 |
| WO | 2009035169 A1 | 3/2009 |
| WO | 2010/038323 | 4/2010 |
| WO | 2010038323 A1 | 4/2010 |
| WO | 2010/125910 | 11/2010 |
| WO | 2010125910 A1 | 11/2010 |

OTHER PUBLICATIONS

Zhu et al. ("Treatment with marine collagen peptides modulates glucose and lipid metabolism in Chinese patients with type 2 diabetes mellitus" Appl Physiol Nutr Metab, Abstract, 2010).*
Ramos-Nino et al. ("Benefits of ACE inhibitors in Diabetes", Clinical Medicine: thereapeutics 2009, vol. 1: 1041-1051).*
Biomaterials Science: An Introduction to Materials in Medicine; Ratner et al., 2013.*
Dictionary.com (http://dictionary.reference.com/browse/prophylaxis, accessed May 13, 2014).*
Merck Manual—Diabetes Mellitus, accessed May 13, 2014.*
Zhu et al. (Appl Physiol Nutr Metab, Abstract, 2010).*
Green et al. (Diabetes Vascular Disease Research 2006;3:159-165).*
Dungan et al. (Clinical Diabetes: vol. 23, (2) 2005).*
Kielgast et al. (Current Diabetes Reviews, 2009,5,266-275).*
Ota, T. et al., Screening and examination of synthesis for DPPIV inhibitory proline-containing peptides, The Japanese Society for Food Science and Technology, Presentation Abstracts for the 57th Meeting, Sep. 1, 2010, 2Ea6.
Harada, N. et al., Experimental Medicine, 2011, vol. 29, No. 5, (special number), pp. 820-835.

(Continued)

*Primary Examiner* — Louise Humphrey
*Assistant Examiner* — Tara Martinez
(74) *Attorney, Agent, or Firm* — Lathrop & Gage LLP; James H. Velema, Esq.

(57) ABSTRACT

A collagen peptide mixture containing three or more kinds selected from Glu-Hyp-Gly, Glu-Hyp, Leu-Hyp-Gly, Pro-Ala, Ser-Hyp, Ala-Hyp-Gly, chemically-modified substances thereof and pharmaceutically acceptable salts thereof, and at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp or a chemically-modified substance thereof or a pharmaceutically acceptable salt thereof have DPPTV inhibitory activity and/or GLP-1 secretion accelerating activity, and hence are effective as a therapeutic or preventive agent or the like for diabetes.

15 Claims, No Drawings

(56) References Cited

OTHER PUBLICATIONS

Ota, T. et al., Screening and examination of synthesis for DPPIV inhibitory proline-containing peptides, The Japanese Society for Food Science and Technology, Presentation Abstracts for the 57th Meeting, Sep. 2, 2010, 2Ea6.

Geraedts, M. et al., Direct induction of CCK and GLP-1 release from murine endocrine cells by intact dietary proteins, Mol. Nutr. Food Res., 2011, vol. 55, pp. 476-484.

Calbet, J. et al., Gastric emptying, gastric secretion and enterogastrone response after administration of milk proteins or their peptide hydrolysates in humans, Eur. J. Nutr., 2004, vol. 43, pp. 127-139.

Hira, T., Food peptide and amino acid that stimulate incretin secretion, Chemistry and Biology, 2011, vol. 49, No. 1, pp. 11-13.

Mochida, T. et al., The Corn Protein, Zein Hydrolysate, Administered into the Ileum Attenuates Hyperglycemia via Its Dual Action on Glucagon-Like Peptide-1 Secretion and Dipeptidyl Peptidase-IV Activity in Rats, Endocrinology, Jul. 2010, vol. 151, No. 7, pp. 3095-3104.

International Search Report for PCT/JP2012/051561, dated Apr. 17, 2012.

Ramos-Nino. 'Benefits of ACE Inhibitors in Diabetes.' Clinical Medicine: Therapeutics. 2009, vol. 1, pp. 1041-1051.

Bauvois. 'A collagen-binding glycoprotein on the surface of mouse fibroblasts is identified as dipeptidyl peptidase IV.' Biochem. J. 1988, vol. 252, pp. 723-731.

Tulipano et al. 'Whey proteins as source of dipeptidyl dipeptidase IV (dipeptidyl peptidase-4) inhibitors.' Peptides. 2011, vol. 32, No. 4, pp. 835-838.

\* cited by examiner

THERAPEUTIC OR PREVENTIVE AGENT FOR DIABETES

TECHNICAL FIELD

The present invention relates to a therapeutic or preventive agent for diabetes. More specifically, the present invention relates to a therapeutic or preventive agent for diabetes containing a peptide obtained by subjecting collagen to a two-step enzymatic treatment.

BACKGROUND ART

Diabetes is a disease with a morbidly elevated blood sugar level, and classified into type 1 diabetes that is caused by insulin depletion due to destruction of pancreatic β cells for some reason, and type 2 diabetes that is caused by impossibility of regulating the blood sugar level despite presence of insulin in the blood. Insulin regulates the blood sugar level by accelerating intake of glucose in skeletal muscle, or suppressing gluconeogenesis in the liver, or accelerating synthesis of glycogen. Glucagon-like peptide-1 (GLP-1) is secreted into blood vessels from L cells existing in the lower small intestine and in the large intestine, and binds with a GLP-1 receptor on a pancreatic β cell, to accelerate insulin secretion. Dipeptidyl peptidase IV (DPPIV) inactivates a target protein by recognizing alanine or proline at the second position from the N terminal of the protein and cutting off the two amino acids. The secreted GLP-1 is inactivated by DPPIV, and only 10 to 15% enters the systemic circulation from the liver through the portal vein (Non-Patent Document 1). Therefore, by inhibiting DPPIV or by accelerating GLP-1 secretion, insulin secretion is accelerated, and the blood sugar level decreases. Hence, a DPPIV inhibitor and a GLP-1 secretion accelerator are recently focused as a therapeutic agent or a preventive agent for diabetes.

As a DPPIV inhibitor, various synthetic pharmaceutical products including sitagliptin are known. However, these are developed in a quest to achieve high drug efficacy primarily for therapy of diabetes, and are associated with side effects such as hypoglycemia. So, peptides obtained by degrading materials for food or drink are conceived. Although these peptides are not so excellent in DPPIV inhibitory activity as synthetic pharmaceutical products, they are very useful in that safety on the human body is ensured, and a side effect will not occur even when they are regularly taken.

Mixtures containing degradation products of materials for food or drink having DPPIV inhibitory activity are described, for example, in the following Patent Documents.

Patent Document 1 describes about a preparation derived from a material for food or drink containing collagen. However, it fails to describe about with what enzyme or in what hydrolysis condition the collagen is degraded to prepare the collagen peptide mixture described in the examples, and lacks any description about what kind of peptide is contained in the collagen peptide mixture.

Patent Document 2 describes that a mixture of degradation products obtained by treating collagen or gelatin with collagenase or the like, followed by treatment with protease has DPPIV inhibitory activity. However, the protease does not have amino peptidase N activity or prolyl tripeptidyl amino peptidase activity possessed by the enzyme used in the second-step enzymatic treatment of the present invention. It also lacks the description about what kind of peptide is contained in the mixture of protease degradation products.

On the other hand, a peptide having DPPIV inhibitory activity is described in the following literatures.

Patent Document 3 describes that twenty-four peptides contained in a water-soluble fraction of cheese have DPPIV inhibitory activity. However, these peptides are long peptides containing five or more amino acids except for one peptide. Patent Document 4 describes that Gly-X-Y-(Gly-Z-W)$_n$ (n is an integer of 0 to 4, X is Pro or Leu, and Y, Z and W each independently represent any amino acids which may be the same or different (excluding Gly)) and the like which are peptides obtained by treating collagen or gelatin with collagenase or the like have DPPIV inhibitory activity. However, these peptides are long peptides containing five or more amino acids except for one peptide. Non-Patent Document 2 describes that a dipeptide and a tripeptide containing proline have DPPIV inhibitory activity, and reports that a dipeptide containing a hydrophobic amino acid on the N terminal side, in particular, has high activity.

The above peptides have a problem of poor intestinal absorptivity.

A mixture containing degradation products of a material for food or drink having GLP-1 secretion accelerating activity is described, for example, in the following literatures.

Patent Document 5 describes about a mixture of papain-degraded products of soybean protein. Non-Patent Document 3 describes that a mixture of hydrolysates of egg protein has GLP-1 secretion accelerating activity, but a mixture of hydrolysates of other proteins failed to exhibit GLP-1 secretion accelerating activity. Non-Patent Document 4 describes a mixture of hydrolysates of whey and casein. Non-Patent Documents 5 and 6 describe that a mixture of hydrolysates of zein originating from corn has GLP-1 secretion accelerating activity and DPPIV inhibitory activity, and the mixture is expected to contain a peptide having GLP-1 secretion accelerating activity and a peptide having DPPIV inhibitory activity.

However, there is no description about what kind of peptide is contained in these mixtures. These literatures lack the description of using collagen as a material for food or drink.

CITATION LIST

Patent Document

PTD 1: Japanese Patent Laying-Open No. 2010-13423
PTD 2: Japanese Patent Laying-Open No. 2009-284798
PTD 3: Japanese Patent Laying-Open No. 2007-39424
PTD 4: WO 2008/066070
PTD 5: Japanese Patent Laying-Open No. 2010-138143

NON PATENT DOCUMENT

NPD 1: Experimental Medicine, Vol. 29, No. 5, (special number), p. 820-835, 2011
NPD 2: Toru Ota et al., "Screening and examination of synthesis for DPPIV inhibitory proline-containing peptide", The Japanese Society for Food Science and Technology, the 57th meeting, Abstract, Sep. 2, 2010, 2Ea6
NPD 3: Mol. Nutr. Food Res., 2011, 55, 476-484
NPD 4: Eur. J. Nutr., (2004) 43: 127-139
NPD 5: Chemistry and Biology, Vol. 49, No. 1, p. 11-13, 2011
NPD 6: Endocrinology, July 2010, 151 (7): 3095-3104

SUMMARY OF INVENTION

Technical Problem

It is an object of the present invention is to provide a therapeutic or preventive agent for diabetes containing a peptide that leads to little side effects, and has high safety and is easily absorbed in the intestinal tract and migrated into a cell. It is also an object of the invention to provide a collagen peptide mixture containing a large quantity of such a peptide, and a method for producing a collagen peptide mixture thereof.

Solution to Problem

As a result of diligent efforts for solving the aforementioned problem, the present inventors found that a collagen peptide mixture obtained by treating collagen or gelatin by a two-step enzymatic treatment, and peptides contained therein surprisingly have DPPIV inhibitory activity and/or GLP-1 secretion accelerating activity. Inventors of the present invention also found that such peptides can be easily absorbed in the intestinal tract and migrated into a cell unlike the conventionally known peptides because almost all of such peptides include Hyp, and are small molecules like a dipeptide or a tripeptide. Further, inventors of the present invention found that a collagen peptide mixture containing a large quantity of such peptides can be produced by the aforementioned production method using a two-step enzymatic treatment by specific combination of enzymes. Based on the findings, inventors of the present invention accomplished the present invention.

That is, the present invention is as follows.

[1] A collagen peptide mixture containing three or more kinds selected from Glu-Hyp-Gly, Glu-Hyp, Leu-Hyp-Gly, Pro-Ala, Ser-Hyp, Ala-Hyp-Gly, chemically-modified substances thereof and pharmaceutically acceptable salts thereof.

[2] The collagen peptide mixture according to [1] containing Glu-Hyp-Gly, Glu-Hyp and Leu-Hyp-Gly.

[3] A therapeutic or preventive agent for diabetes containing the collagen peptide mixture according to [1] or [2].

[4] A DPPIV inhibitor containing the collagen peptide mixture according to [1] or [2].

[5] A GLP-1 secretion accelerator containing the collagen peptide mixture according to [1] or [2].

[6] A therapeutic or preventive agent for diabetes containing at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof.

[7] A DPPIV inhibitor containing at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp and Ser-Hyp-Gly, or a chemically-modified substance thereof, or a pharmaceutically acceptable salt thereof.

[8] A GLP-1 secretion accelerator containing at least one peptide selected from the group consisting of Glu-Hyp-Gly, Glu-Hyp, Leu-Hyp-Gly, Pro-Ala, Ser-Hyp, Ala-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof.

[9] A peptide selected from the group consisting of Glu-Hyp and Glu-Hyp-Gly, or a chemically-modified substance thereof, or a pharmaceutically acceptable salt thereof.

[10] A method for producing a collagen peptide mixture containing at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp, by subjecting collagen or gelatin to a two-step enzymatic treatment, wherein an enzyme used in a primary enzymatic treatment is selected from the group consisting of collagenase, thiol protease, serine protease, acidic protease, alkaline protease and metal protease, and an enzyme used in a secondary enzymatic treatment is an enzyme having aminopeptidase N activity, or an enzyme having both aminopeptidase N activity and prolyl tripeptidyl aminopeptidase activity, or a combination of an enzyme having aminopeptidase N activity and an enzyme having prolyl tripeptidyl aminopeptidase activity.

[11] The collagen peptide mixture according to [1] or [2], for treating or preventing diabetes.

[12] At least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof, for treating or preventing diabetes.

[11] At least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp and Ser-Hyp-Gly, or a chemically-modified substance thereof, or a pharmaceutically acceptable salt thereof, for inhibiting DPPIV.

[12] At least one peptide selected from the group consisting of Glu-Hyp-Gly, Glu-Hyp, Leu-Hyp-Gly, Pro-Ala, Ser-Hyp, Ala-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof, for accelerating GLP-1 secretion.

[13] A method for treating or preventing diabetes comprising administering the collagen peptide mixture according to [1] or [2] to a subject (preferably, a patient) in need of the same.

[14] A method for treating or preventing diabetes comprising administering at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof to a subject (preferably, a patient) in need of the same.

[15] A method for inhibiting DPPIV comprising administering at least one peptide selected from the group consisting of Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp and Ser-Hyp-Gly, or a chemically-modified substance thereof, or a pharmaceutically acceptable salt thereof to a subject (preferably, a patient) in need of the same.

[16] A method for accelerating GLP-1 secretion comprising administering at least one peptide selected from the group consisting of Glu-Hyp-Gly, Glu-Hyp, Leu-Hyp-Gly, Pro-Ala, Ser-Hyp, Ala-Hyp-Gly, Gly-Pro-Hyp, (Pro-Hyp-Gly)$_5$, Pro-Hyp, Hyp-Gly, Pro-Gly, Pro-Pro and Ala-Hyp, or a chemically-modified substance thereof, or a pharmaceutically acceptable salt thereof to a subject (preferably, a patient) in need of the same.

The peptide used in the present invention is also simply referred to as a "specific peptide". Three letter codes for amino acid units forming the aforementioned peptide molecule are also indicated by one letter codes. Concretely, they are abbreviated in the following ways: Leu=L, Hyp=O, Gly=G, Pro=P, Ala=A, Glu=E, Ile=I, Ser=S, F=Phe.

Advantageous Effects of Invention

The therapeutic or preventive agent for diabetes, the DPPIV inhibitor and the GLP-1 secretion accelerator according to the present invention are also suited for oral administration because they will not lead to side effects, they have high safety and resistance to digestive enzymes, and they are easily absorbed into a body in the intestinal tract and migrated into a cell. Also, according to the method for producing a collagen peptide mixture of the present invention, it is possible to obtain a collagen peptide mixture containing a large quantity of the aforementioned specific peptide effectively and reliably.

DESCRIPTION OF EMBODIMENTS

In the following, the therapeutic or preventive agent for diabetes, the DPPIV inhibitor, the GLP-1 secretion accelerator and the methods for producing a collagen peptide mixture according to the present invention will be specifically described, however, the scope of the present invention is not restricted by these descriptions, and those other than the following exemplification may be practiced while they are appropriately modified without departing from the subject matter of the present invention.

1. Collagen Peptide Mixture and Specific Peptide

The collagen peptide mixture of the present invention is a collagen peptide mixture containing three or more kinds selected from EOG, EO, LOG, PA, SO, AOG, chemically-modified substances thereof and pharmaceutically acceptable salts thereof. The three or more peptides contained in the present collagen peptide mixture preferably include any one of EOG, EO and LOG, more preferably include EOG or LOG, and particularly preferably include LOG. The total weight of three or more kinds selected from EOG, EO, LOG, PA, SO, AOG, chemically-modified substances thereof and pharmaceutically acceptable salts thereof is preferably 2% by weight or more, more preferably 3% by weight or more, further preferably 4% by weight or more, relative to the collagen peptide mixture.

The specific peptide used in the present invention is selected from the group consisting of EOG, EO, LOG, PA, SO, AOG, POG, LO, IO, SOG, GPO, (POG)$_5$, PO, OG, PG, PP and AO. EOG, EO, LOG, PA, SO, AOG, POG, LO, IO and SOG have DPPIV inhibitory activity, and EOG, EO, LOG, PA, SO, AOG, GPO, (POG)$_5$, PO, OG, PG, PP and AO have GLP-1 secretion accelerating activity. EOG, EO, LOG, PA, SO and AOG are preferred peptides because they have both DPPIV inhibitory activity and GLP-1 secretion accelerating activity. More preferred peptides are EOG, EO and LOG, and further preferred are EOG and LOG, and particularly preferred is LOG.

The specific peptide may be prepared, for example, by a synthetic method from amino acids, or by a method of subjecting collagen or gelatin to a two-step enzymatic treatment as will be described later. However, other methods may be used for preparation, and for example, a method omitting a primary enzymatic treatment, or a method of conducting a primary enzymatic treatment and a secondary enzymatic treatment concurrently may be applicable in place of the following two-step enzymatic treatment method.

<Synthesis from Amino Acids>

The specific peptide may be synthesized from amino acids. As a method for synthesizing the specific peptide from amino acids, generally, (1) a solid-phase synthesis method and (2) a liquid-phase synthesis method (for example, see Japanese Laid-Open Patent Publication No. 2003-183298) are known, and in the case of the former method, (A) Fmoc method and (B) Boc method are further known, and the specific peptide may be synthesized in any method.

Detailed description will be made while taking a solid-phase method as one example. It may be synthesized by a known solid-phase synthesis method wherein proline is immobilized to a carrier polystyrene, and a Fmoc group or a Boc group is used for protection of an amino group. That is, by a dehydration reaction using a bead of polystyrene polymer gel having a diameter of about 0.1 mm whose surface is modified with an amino group as a solid phase, and diisopropylcarbodiimide (DIC) as a condensing agent, hydroxyproline is bound to proline whose amino group is protected by a Fmoc (fluorenyl-methoxy-carbonyl) group (to form a peptide bond), and the solid phase is washed well with a solvent, to remove the remaining hydroxyproline or the like. Thereafter, the protective group of proline bound to the solid phase is removed (deprotected), and thus PO can be synthesized. Subsequently, in a similar manner, by making glycine bind to an amino group of hydroxyproline of the PO (to form a peptide bond), POG can be obtained. In this way, by making amino acids bind sequentially, the intended peptide can be synthesized.

<Chemical Modification>

In the specific peptide, an amino group or a carboxyl group of a constituent amino acid may be chemically modified, and as to hydroxyproline, a hydroxyl group may be chemically modified. By this chemical modification, it is possible to improve the solubility in the weakly acidic to neutral condition, and to improve the compatibility with other DPPIV inhibitors. Concretely, examples include chemical modification such as O-acetylation for a hydroxyl group in hydroxyproline, chemical modification such as esterification or amidation for an α-carboxyl group in glycine, chemical modification such as polypeptidylation, succinylation, maleylation, acetylation, deamination, benzoylation, alkylsulfonylation, allylsulfonylation, dinitrophenylation, trinitrophenylation, carbamylation, phenylcarbamylation or thiolation for an α-amino group in proline. Appropriate chemical modification may be selected depending on the kind or the like of other DPPIV inhibitors. The specific peptide may be rendered basic by ethylenediamination, spermination or the like.

As a concrete means and treatment condition of chemical modification of the specific peptide, a usual chemical modification technique for peptide is applied. As to chemical modification of a hydroxyl group in hydroxyproline, for example, O-acetylation may be achieved by treatment with acetic anhydride in an aqueous solvent or in a non-aqueous solvent. As to chemical modification of an α-carboxyl group of glycine, for example, esterification may be achieved by aerating a suspension in methanol with a dry hydrogen chloride gas, and amidation may be achieved by treatment with carbodiimide. As other concrete examples of chemical modification, chemical modification techniques described in Patent Publication No. 62-44522, Patent Publication No. 5-79046 and so on may be applied.

<Pharmaceutically Acceptable Salt>

Examples of the pharmaceutically acceptable salt include inorganic acid salts such as hydrochlorides, sulfates, phosphates and hydrobromides, organic acid salts such as acetates, methanesulfonates, benzenesulfonates, p-toluenesulfonates, succinates, oxalates, fumarates and maleates, inorganic basic salts such as sodium salts, potassium salts and calcium salts, and organic basic salts such as triethylammonium salts. The specific peptide may be rendered a pharmaceutically acceptable salt according to an ordinary method.

2. Method for Producing Collagen Peptide Mixture

By a method of subjecting collagen or gelatin to a two-step enzymatic treatment, a collagen peptide mixture can be produced. Also, by further purifying the prepared collagen peptide mixture, the specific peptide can be produced.

In this enzymatic treatment method, it is possible to obtain the collagen peptide mixture containing the specific peptide, concretely by a two-step enzymatic treatment including a primary enzymatic treatment on collagen or gelatin by a commonly used method, and a secondary enzymatic treatment using an enzyme having aminopeptidase N activity, or an enzyme having both aminopeptidase N activity and prolyl tripeptidyl aminopeptidase activity, or a combination of an enzyme having aminopeptidase N activity and an enzyme having prolyl tripeptidyl aminopeptidase activity.

Examples of the material collagen include, but are not limited to, collagen derived from mammals such as cows and pigs, and collagen derived from fish such as shark and sea bream. These may be obtained from the bone or skin part of the mammals, or from the bone, skin or scale part of the fish. Concretely, the bone, skin or scale may be subjected to conventionally known treatments such as a delipidation and decalcification treatment, an extraction treatment and the like. The material gelatin may be obtained by treating the collagen by a conventionally known method such as extraction with hot water.

<Primary Enzymatic Treatment>

As the enzyme used in the primary enzymatic treatment, any enzymes capable of cutting peptide bonds in collagen or gelatin may be used without particular limitation, however, an enzyme called proteolytic enzyme or protease is typically used. Concretely, examples include collagenase, thiol protease, serine protease, acidic protease, alkaline protease, and metal protease, which may be used singly or in combination of plural kinds. As the thiol protease, for example, plant derived proteases such as chymopapain, papain, bromelain and ficin, and animal derived proteases such as cathepsin and calcium-dependent protease are known. As the serine protease, trypsin, cathepsin D and so on are known, and as the acidic protease, pepsin, chymotrypsin and the like are known. As the enzyme for use, it is preferred to use enzymes other than enzymes derived from pathogenic microorganisms, from the view point of application of the prepared collagen peptide mixture and the specific peptide to pharmaceuticals, foods for specified health use and the like.

As a treatment condition of the primary enzymatic treatment, for example, the treatment may be effected at 30 to 65° C. for 1 to 72 hours using 0.1 to 5 parts by weight of enzyme per 100 parts by weight of collagen or gelatin. The average molecular weight of the collagen peptide mixture obtained by the primary enzymatic treatment of the collagen or gelatin is preferably 500 to 2000, and more preferably 500 to 1800. The average molecular weight falling within the above range implies that peptides having a relatively large molecular weight are adequately generated. While the enzyme may be inactivated as necessary after the primary enzymatic treatment, the inactivation temperature in this case is for example, 70 to 100° C.

<Secondary Enzymatic Treatment>

As the enzyme used in the secondary enzymatic treatment, an enzyme having aminopeptidase N activity, or an enzyme having both aminopeptidase N activity and prolyl tripeptidyl aminopeptidase activity, or a combination of an enzyme having aminopeptidase N activity and an enzyme having prolyl tripeptidyl aminopeptidase activity is included. Here, "aminopeptidase N activity" is basically a peptidase that liberates an amino acid from the N terminal of a peptide chain, and acts when there is an amino acid other than proline or hydroxyproline at the second position from the N terminal. In addition, "prolyl tripeptidyl aminopeptidase activity" means a peptidase that liberates three residues on the N terminal, from a substrate having proline or hydroxyproline at the third position from the N terminal. From the view point of application of the prepared collagen peptide mixture and the specific peptide to pharmaceuticals, foods for specified health use and the like, it is preferred to use an enzyme other than enzymes derived from pathogenic microorganisms. Concretely, as an enzyme having aminopeptidase N activity, for example, aminopeptidase N (EC3.4.11.2; Yoshimoto, T., et al., Agric. Biol. Chem., 52: 217-225 (1988) or the like) is included. Further, as an enzyme having prolyl tripeptidyl aminopeptidase activity, for example, prolyltripeptidyl aminopeptidase (EC3.4.14.-; Banbula, A., et al., J. Biol. Chem., 274: 9246-9252, (1999) or the like) is included.

In the secondary enzymatic treatment, an enzymatic reaction using the aforementioned enzyme, for example, using an enzyme having aminopeptidase N activity and an enzyme having prolyl tripeptidyl aminopeptidase activity derived from *Aspergillus* is conducted. By this reaction, the specific peptide that is not contained in the primary enzymatic treatment product is generated.

As a treatment condition of the secondary enzymatic treatment, for example, the treatment may be effected at 30 to 65° C. for 1 to 72 hours using 0.01 to 5 parts by weight of enzyme per 100 parts by weight of the product of the primary enzymatic treatment. An average molecular weight of the collagen peptide mixture obtained by the secondary enzymatic treatment is preferably 500 to 1800, and more preferably 500 to 1500. This secondary enzymatic treatment is principally intended to generate a peptide molecule having a specific structure, and it is preferred to conduct the secondary enzymatic treatment so that the average molecular weight falls within the aforementioned range for preventing relatively large peptides in the collagen peptide mixture obtained by the primary enzymatic treatment from being excessively hydrolyzed. It is necessary to inactivate the enzyme after the secondary enzymatic treatment, and the inactivation temperature is for example, 70 to 100° C.

Further, as the enzyme used in the secondary enzymatic treatment, an enzyme having different activity besides the aminopeptidase N activity or prolyl tripeptidyl aminopeptidase activity may be used, or an enzyme having different activity may be used together, depending on the purpose such as degradation of the side product, the kind of the material collagen, and the kind of the enzyme used in the primary enzymatic treatment.

As such different activity, for example, dipeptidase activity such as prolidase activity or hydroxyprolidase activity may be allowed to act, to thereby decompose the byproduct dipeptide. Further, since the aminopeptidase N activity basically liberates amino acids on the N terminal side one by one, decomposition in the primary enzymatic treatment may be insufficient depending on the kind of collagen that is a starting material or the kind of the enzyme used in the primary enzymatic treatment, and thus the time required for the secondary enzymatic treatment may be prolonged. For addressing this, for example, another activity such as activity of prolylolligopeptidase that is endopeptidase that hydrolyzes the carboxyl group side of proline may be allowed to act, to thereby cut and remove the unnecessary site as a lump of oligopeptide or the like. In this manner, it is possible to conduct the secondary enzymatic treatment more efficiently.

<Two-Step Enzymatic Treatment>

The details of the two-step enzymatic treatment will be described. First, by the primary enzymatic treatment, a peptide having a relatively large molecular weight that is useful for reduction of inflammation in bone and cartilage tissues mediated by an oral immune tolerance mechanism, for example, [$X_1$-Gly-$X_2$-Hyp-Gly-Pro] ($X_1$ and $X_2 \neq$Hyp) is generated.

In the subsequent secondary enzymatic treatment, proline on the C terminal is liberated by the action of aminopeptidase N activity on the [$X_1$-Gly-$X_2$-Hyp-Gly-Pro], and [$X_1$-Gly-$X_2$-Hyp-Gly] is generated, or $X_1$ on the N terminal is further liberated and [Gly-$X_2$-Hyp-Gly] is obtained.

Further, aminopeptidase N activity acts on the [$X_1$-Gly-$X_2$-Hyp-Gly] to cleave the peptide bond between glycine and $X_2$, so that a specific peptide [$X_2$-Hyp-Gly] ($X_2$=Leu, Pro, Glu, Ser or Ala) is obtained.

Also, prolyl tripeptidyl aminopeptidase activity acts on the [Gly-$X_2$-Hyp-Gly] to cleave the peptide bond between hydroxyproline and glycine, to give [Gly-$X_2$-Hyp], and then aminopeptidase N activity acts to cleave the peptide bond between glycine and $X_2$, to give a specific peptide [$X_2$-Hyp] ($X_2$=Leu, Glu, Ile or Ser).

It is preferred to allow both aminopeptidase N activity and prolyl tripeptidyl aminopeptidase activity to act, because a dipeptide having excellent intestinal tract absorptivity among the specific peptides of the present invention can be efficiently obtained.

The enzyme used in Patent Document 2, for example, protease N "AMANO" G does not include an enzyme having aminopeptidase N activity or an enzyme having prolyl tripeptidyl aminopeptidase activity. So, we prepared a peptide mixture (CPT-Cont) in the same condition as that in Example 1 (HACP-01-N) of Patent Document 2, and analyzed the mixture by a LC-MS/MS analysis method, however, the mixture did not contain a specific peptide other than GPO (see, Comparative Example 2).

<Purification of Collagen Peptide Mixture>

By the aforementioned two-step enzymatic treatment, and fermentation additionally conducted as necessary, a collagen peptide mixture can be prepared. However, since the collagen peptide mixture contains amino acids and peptides other than the specific peptide, it may be purified by a conventionally known method as is necessary. Examples of the purification method include ultrafiltration and various kinds of liquid chromatography methods such as gel filtration chromatography, ion exchange chromatography, reverse-phase chromatography and affinity chromatography.

By fractionation and purification of the collagen peptide mixture, the specific peptide can be obtained. The method for fractionation and purification is not limited, and any conventionally known methods, for example, ultrafiltration, and various liquid chromatography methods such as gel filtration chromatography, ion exchange chromatography, reverse-phase chromatography and affinity chromatography, and combination of these methods may be mentioned. Concretely, the fractionation and purification may be conducted, for example, in the following manner. To be more specific, first, about 2 g/10 mL of the collagen peptide mixture is applied to an ion exchange column (for example, DEAE TOYOPEARL 650M column (manufactured by TOSOH CORPORATION) or SP TOYOPEARL 650M column (manufactured by TOSOH CORPORATION)) in two parts, and a void volume fraction eluted with distilled water is collected. Then, the collected fraction is applied to a column having an ion exchange group of opposite polarity to the foregoing ion exchange column (for example, SP TOYOPEARL 650M column (manufactured by TOSOH CORPORATION) or DEAE TOYOPEARL 650M column (manufactured by TOSOH CORPORATION)), and a void volume fraction eluted with distilled water is collected. Next, the fraction is applied to a gel filtration column (for example, Sephadex LH-20 column (manufactured by Pharmacia) etc.), and eluted with an aqueous 30% methanol solution and a fraction corresponding to the position where a specific peptide which is a chemically synthesized substance is eluted is collected. This fraction is applied to a high performance liquid chromatography (HPLC) loaded with a reverse-phase column (for example, μBondasphere 5 μC18 300 angstroms column (manufactured by Waters) etc.), and fractionated by a straight concentration gradient of a 32% or less aqueous acetonitrile solution containing 0.1% trifluoroacetic acid. Then the collected specific peptide fraction is dried to solid under reduced pressure, and thereby a specific peptide with high purity can be obtained.

3. Therapeutic or Preventive Agent for Diabetes

The collagen peptide mixture, the specific peptide and so on according to the present invention have DPPIV inhibitory activity and/or GLP-1 secretion accelerating activity, and can be used as a therapeutic or preventive agent for diabetes. Here, a therapeutic or preventive agent for diabetes means a pharmaceutical that is used for therapy and/or prevention of diabetes. Also, the collagen peptide mixture, the specific peptide and so on may be used while they are contained in foods for specified health use, healthy foods, and various food materials.

A therapeutic or preventive agent for diabetes containing a collagen peptide mixture, a specific peptide and so on may be administered orally or parenterally in preparations of various forms. The forms include, for example, tablet, granule, capsule, powdered drug, powder, liquid, injection, transdermal agent, suppository, nasal drop, inhalant and so on, and preferably include orally administered tablet, granule, capsule and the like, and parenterally administered injection, transdermal agent and the like. The administration amount of the collagen peptide mixture, the specific peptide and so on differs depending on the condition and body weight of a patient, the kind of the compound, the administration route and the like. In the case of oral administration, the administration amount per day per adult is, for example, about 0.1 to 1000 mg, preferably about 1 to 500 mg, and more preferably about 10 to 200 mg. In the case of an injection, the administration amount is, for example, about 0.01 to 200 mg, preferably about 0.1 to 100 mg, and more preferably about 1 to 50 mg. For preparations of other forms, the amount can be appropriately determined with reference to these administration amounts. These preparations may be administered once or several times per day, or once per one to several days. In the case of oral administration, it is possible to control the blood sugar level within a normal range by administration before meal. The specific peptide, in particular, a peptide containing Hyp is suitably taken by oral administration because it is little degraded into amino acids due to its high tolerance to digestive enzymes, and is rapidly absorbed into blood from the intestinal tract, or directly absorbed into an intestinal tract surface cell or a L cell from the intestinal tract.

Examples of pharmaceutical carriers for orally-administered preparation include those commonly used, such as excipients (crystalline cellulose, lactose, sugar, cornstarch, potassium phosphate, sorbit, glycine, etc.), binders (syrup, gum arabic, gelatin, sorbit, tragacanth, polyvinylpyrrolidone, etc.), lubricants (magnesium stearate, talc, polyethylene glycol, silica, etc.), disintegrants (potato starch, etc.) and humectants (sodium lauryl sulfate, etc.). In the case of the orally-administered preparation, a mixture of the collagen peptide mixture, the specific peptide or the like, and the aforementioned pharmaceutical carrier may be prepared into a tablet by tablet compression molding, or prepared into any other forms such as solid preparations including granules, powders and capsules, liquid preparations including solutions, suspensions and emulsions, and lyophilized preparations by conventionally known methods. In this case, it is preferred to combine the specific peptide in a proportion of 0.001 parts by weight or more, to the whole amount of the preparation. More preferably, it is combined in a proportion of 0.01 parts by weight or more. With a proportion of less than 0.001 parts by weight, the effect of the present invention cannot be sufficiently expressed.

In the case of parenteral administration, for example, preparations such as injections, drops and suppositories may be obtained using distilled water for injection, saline or an aqueous glucose solution. In the case of injection into vein, a collagen peptide mixture, the specific peptide or the like diluted in saline or the like is used, in such a concentration that the content of peptide molecules having a specific structure is preferably 0.1 mol/L or more, as described above. Further, the content of the specific peptide is preferably 10 μmol/L or more.

<Other Active Ingredients>

A therapeutic or preventive agent for diabetes containing the collagen peptide mixture, the specific peptide and so on of the present invention may be combined with other active ingredients if necessary, as far as the effect of the present invention is not interfered. Examples of other active ingredients include other therapeutic agents for diabetes (insulin, sulfonylurea, biguanide, α-glucosidase inhibitor, insulin resistance improving agent, insulin secretion accelerator, GLP-1 analog and the like). In this case, it may be used as a combined agent, or may be used together.

4. DPPIV Inhibitor/GLP-1 Secretion Accelerator

The DPPIV inhibitor of the present invention is used as a therapeutic or preventive agent for diabetes as described above. In addition to this, the present DPPIV inhibitor can be used, for example, for therapy and prevention of central nervous system diseases such as attack, ischemia, Parkinson's disease and migraine, immune and autoimmune diseases such as arthritis and chronic rheumatoid arthritis, tumor and so on (National Patent Publication No. 2004-534836, and Sumiko Tanaka et al., "Effect of suppressing arthritis onset by dipeptidyl peptidase IV inhibitor", Inflammation, Vol. 18, No. 3, May 1998).

The GLP-1 secretion accelerator of the present invention is used as a therapeutic or preventive agent for diabetes as described above. In addition to this, the present GLP-1 secretion accelerator further has a surfactant secretion accelerating action in lung, a myocardium protecting action and a cardiac function improving action in heart, a neuronal cell protecting action, a memory increasing action and an appetite regulating action in brain, a stomach excretion decreasing action in gastrointestinal tract, a sodium regulating action in kidney and so on. Hence, it may be used for therapy or prevention of diseases requiring these actions, for example, obesity and neurodegenerative conditions (Alzheimer's disease, Parkinson's disease, Huntington's disease, amyotrophic lateral sclerosis, apoplexy, multiple sclerosis, brain injury, spine injury, peripheral neuropathy and so on) (Non-Patent Document 1 and Japanese Patent Laying-Open No. 2010-90129).

EXAMPLES

In the following, the present invention will be described more concretely for a collagen peptide mixture, a specific peptide and so on contained in a therapeutic or preventive agent for diabetes according to the present invention by their performance evaluation tests and formulation examples, however, the present invention is not limited to these. In the following, "part by weight" can be merely indicated by "part", and "% by weight" can be merely indicated by "%" for convenience.

[Preparation of Specific Peptide]

Specific peptides used in the later-described performance evaluation tests and formulation examples were synthesized by the solid-phase method as described above.

To be more specific, first, by a dehydration reaction using a bead of polystyrene polymer gel having a diameter of about 0.1 mm whose surface was modified by an amino group as a solid phase, and 10 parts of diisopropylcarbodiimide (DIC) as a condensing agent, 45 parts of alanine was caused to bind (peptide bond) with 45 parts of proline whose amino group was protected by a Fmoc (fluorenyl-methoxy-carbonyl) group, and then the solid phase was washed well with a solvent (ethyl alcohol) to remove the remaining proline and the like. Then the protecting group of proline binding with the solid phase was removed (deprotected) by immersion in warm trifluoroacetic acid, and thus PA was synthesized.

For synthesis of the peptide molecule, a Liberty peptide synthesis system (manufactured by CEM Corporation) was used.

In a similar manner, LO, EO, IO, SO, LOG, POG, EOG, SOG, AOG, AO, GPO, (POG)$_5$, PO, OG, PG and PP were synthesized. As will be specifically described, [m/z] of EO and EOG were measured by using LC-MS/MS, and 261.1>132.0 for EO, and 318.1>225.0 for EOG.

[Preparation of Other Peptides]

As other peptides for comparison for use in the later-described performance evaluation tests and formulation examples, peptides of PAG, FO and IOG were synthesized by a solid-phase method in a similar manner to that for the aforementioned specific peptide.

Example 1

Preparation of Collagen Peptide Mixture Containing Specific Peptide, 1

A collagen peptide mixture (CPT-PU) derived from pig skin containing a specific peptide for use in the later-described performance evaluation tests and formulation examples was obtained in the following manner.

To be more specific, 1 kg of gelatin (type I collagen) which is a thermal-denatured product of collagen derived from pig skin was dissolved in 4 L of hot water at 75° C., and the temperature was modulated to 60° C., and then as a primary reaction, 10 g of protease derived from yellow *Aspergillus* was added, and the reaction was retained at pH 5.0 to 6.0 at a temperature of 45 to 55° C. for 3 hours, to conduct an enzymatic hydrolysis treatment. Then, as a secondary enzymatic reaction, each 7.5 g of aminopeptidase N (EC3.4.11.2) and prolyl tripeptidyl aminopeptidase (EC3.4.14.-) derived from *Aspergillus oryzae* were added, and solubilized, and then allowed to react at 50° C. for 5 hours. After the reaction, the reaction liquid was heated at 100° C. for 10 minutes, and then cooled to 60° C., and filtered by using activated charcoal and a filtration aid (diatomaceous earth), and the obtained mother liquor was subjected to a high temperature sterilization treatment at 120° C. for 3 seconds. Then, the mother liquor after sterilization was spray-dried, to obtain a collagen peptide mixture (CPT-PU) derived from pig skin.

This CPT-PU was subjected to thin-layer chromatography (TLC). To be more specific, 10 μg of water-solubilized CPT-PU was added dropwise (spot origin) to a TLC plate (trade name "Cellulose F", manufactured by Merck) and dried, and then developed with a solvent (n-butanol:acetic acid:water=4:1:2). An isatin-Zn coloring liquid was sprayed, and by confirming that the chromogenic Rf value of a blue spot coincides with the Rf value of the synthetic peptide POG on the same plate, the CPT-PU was determined to contain the peptide.

For the above CPT-PU, a LC-MS/MS analysis was further conducted. However, since the CPT-PU was difficult to be analyzed because it contained many kinds of peptides, after fractioning and collecting the sample by reverse-phase chromatography by a Sep-PakC18 cartridge column (manufactured by Waters), followed by lyophilization, the resultant sample was dissolved in 20 μL of MQ water, and subjected to a LC-MS/MS analysis.

The above analysis demonstrated that the CPT-PU further contains peptides LOG, EOG, SOG, AOG and PA.

The quantitative analysis by LC-MS/MS demonstrated that the CPT-PU contains 4% of PA, each 2% of AOG and POG, and each 1.5% of LOG, EOG and SOG.

Here, a quantitative analysis by LC-MS/MS was conducted in the following manner.

As a HPLC apparatus, "NANOSPACE SI-2" (manufactured by SHISEIDO) was used. This apparatus is equipped with a column: Hypersil GOLD PFP 2.1×150 mm, 5 μm. A linear gradient between mobile phases: (A) aqueous solution containing 0.2% formic acid and 2 mM ammonium acetate and (B) methanol was employed at an injection amount of 1 μL and a column temperature of 40° C. A MS/MS (tandem type mass spectrometry: TSQ Vantage, Thermo Fisher Scientific Inc.) system coupled thereto was used in the following conditions. Concretely, using an ionization method (positive ESI), SRM conditions were set as follows (herein, indicated by [m/z]): 302.2>189.4 for LOG; 286.1>189.3 for POG; 187.1>70.3 for PA; 261.1>132.0 for EO; 245.1>132.3 for LO; 245.2>132.1 for IO; 318.1>225.4 for EOG; 276.1>189.4 for SOG; 219.1>132.2 for SO; and 260.1>189.4 for AOG.

Example 2

Preparation of Collagen Peptide Mixture Containing Specific Peptide, 2

A collagen peptide mixture (CPT-P-H) derived from fish scale containing a specific peptide for use in the later-described performance evaluation tests and formulation examples was obtained in a similar manner to the production of the CPT-PU except that gelatin derived from fish scale was used.

The CPT-P-H was analyzed by TCL in a similar manner to the case of the CPT-PU, and existence of a peptide POG was confirmed.

Further, the LC-MS/MS analysis revealed that the CPT-P-H further contains peptides LOG, EOG, SOG, AOG, and PA.

The quantitative analysis by LC-MS/MS demonstrated that the CPT-P-H contains 2.5% of PA, each 2% of SOG, LOG and AOG, 1.5% of POG, and 1% of EOG.

Example 3

Preparation of Collagen Peptide Mixture Containing Specific Peptide, 3

A collagen peptide mixture (CPT-P-20) derived from pig skin containing a specific peptide for use in the later-described performance evaluation tests and formulation examples was obtained in the following manner.

To be more specific, 1 kg of gelatin (type I collagen) which is a thermal-denatured product of collagen derived from pig skin was dissolved in 4 L of 20 mM Tris-HCl buffer (pH 7.5) under warming, and cooled to 40° C., and then as a primary enzymatic reaction, 1 g of collagenase (manufactured by NITTA GELATIN INC., Collagenase N2) was added, and the reaction was retained at pH 7.0 to 7.8, at 40° C. for 24 hours, to conduct an enzymatic degradation treatment. Then as a secondary enzymatic reaction, each 10 g of aminopeptidase N (EC3.4.11.2) and prolyl tripeptidyl aminopeptidase (EC3.4.14.-) derived from *Aspergillus niger* were added to this reaction liquid and solubilized, and then allowed to react at pH 4.0, 50° C. for 5 hours. After the reaction, the reaction liquid was heated at 100° C. for 10 minutes, and then cooled to 60° C., and filtered by using activated charcoal and a filtration aid (diatomaceous earth), and the obtained mother liquor was subjected to a high temperature sterilization treatment at 120° C. for 3 seconds. Then, the mother liquor after sterilization was spray-dried, to obtain CPT-P-20.

The CPT-P-20 was analyzed by TLC in a similar manner to the case of the CPT-PU, and existence of a peptide POG was confirmed.

Also, the LC-MS/NIS analysis revealed that the CPT-P-20 further contains peptides PA, LOG, AOG, EOG, SOG, EO, LO, IO and SO.

The quantitative analysis by LC-MS/NIS demonstrated that the CPT-P-20 contains 3% of PA, 2.5% of LOG, 2% of EOG, 1% of AOG, and each 0.5% of POG, SOG, EO, LO, IO and SO.

Example 4

Preparation of Collagen Peptide Mixture Containing Specific Peptide, 4

A collagen peptide mixture (CPT-P-22) derived from pig skin containing a specific peptide for use in the later-described performance evaluation tests and formulation examples was obtained in the following manner.

To be more specific, 1 kg of gelatin (type 1 collagen) which is a thermal-denatured product of collagen derived from pig skin was dissolved in 4 L of 20 mM Tris-HCl buffer (pH 7.5) under warming, and cooled to 40° C., and then as a primary enzymatic reaction, 1 g of collagenase (manufactured by NITTA GELATIN INC., Collagenase N2) was added, and the reaction was retained at pH 7.0 to 7.8, at 40° C. for 24 hours, to conduct an enzymatic degradation treatment. Then as a secondary enzymatic reaction, each 10 g of aminopeptidase N (EC3.4.11.2) and prolyl tripeptidyl aminopeptidase (EC3.4.14.-) derived from *Aspergillus oryzae* were added to this reaction liquid and solubilized, and then allowed to react at pH 4.0, 50° C. for 3 hours. After the reaction, the reaction liquid was heated at 100° C. for 10 minutes, and then cooled to 60° C., and filtered by using activated charcoal and a filtration aid (diatomaceous earth), and the obtained mother liquor was subjected to a high temperature sterilization treatment at 120° C. for 3 seconds. Then, the mother liquor after sterilization was spray-dried, to obtain CPT-P-22.

The CPT-P-22 was analyzed by TLC in a similar manner to the case of the CPT-PU, and existence of a peptide POG was confirmed.

Also, the LC-MS/NIS analysis revealed that the CPT-P-22 further contains peptides LOG, EOG, SOG, AOG, EO, LO, IO and PA.

The quantitative analysis by LC-MS/NIS demonstrated that the CPT-P-22 contains 3% of PA, 2.5% of LOG, each 1% of POG, AOG and EOG, and each 0.5% of SOG, EO, LO and JO.

Example 5

Preparation of Collagen Peptide Mixture Containing Specific Peptide, 5

A collagen peptide mixture (CPT-P-25) derived from pig skin containing a specific peptide for use in the later-described performance evaluation tests and formulation examples was obtained in the following manner.

To be more specific, 1 kg of gelatin (type 1 collagen) which is a thermal-denatured product of collagen derived from pig skin was dissolved in 4 L of 20 mM Tris-HCl buffer (pH 7.5) under warming, and cooled to 40° C., and then as a primary enzymatic reaction, 1 g of collagenase (manufactured by NITTA GELATIN INC., Collagenase N2) was added, and the reaction was retained at pH 7.0 to 7.8, at 40° C. for 24 hours, to conduct an enzymatic degradation treatment. Then as a secondary enzymatic reaction, each 7.5 g of aminopeptidase N (EC3.4.11.2) and prolyl tripeptidyl aminopeptidase (EC3.4.14.-) derived from *Aspergillus niger* were added to this reaction liquid and solubilized, and then allowed to react at pH 4.0, 50° C. for 3 hours. After the reaction, the reaction liquid was heated at 100° C. for 10 minutes, and then cooled to 60° C., and filtered by using activated charcoal and a filtration aid (diatomaceous earth), and the obtained mother liquor was subjected to a high temperature sterilization treatment at 120° C. for 3 seconds. Then, the mother liquor after sterilization was spray-dried, to obtain CPT-P-25.

The CPT-P-25 was analyzed by TLC in a similar manner to the case of the CPT-PU, and existence of a peptide POG was confirmed.

Also, the LC-MS/MS analysis revealed that the CPT-P-25 further contains peptides LOG, EOG, SOG, AOG, EO, LO and PA.

The quantitative analysis by LC-MS/MS demonstrated that the CPT-P-25 contains 4% of POG, 2.5% of PA, 1% of LOG, and each 0.5% of AOG, EOG, SOG, EO and LO.

Example 6

Preparation of Collagen Peptide Mixture Containing Specific Peptide, 6

A collagen peptide (CPT-PP) derived from fish scale was obtained in similar operations to those in production of CPT-P-U in Example 2 except that 20 g of actinidin derived from kiwi fruit (EC3.4.22.14) was used in the primary reaction.

The CPT-PP was analyzed by TCL in a similar manner to the case of the CPT-PU, and existence of a peptide POG was observed.

Further, the LC-MS/MS analysis revealed that the CPT-PP further contains peptides LOG, EOG, SOG, AOG, EO and PA.

The quantitative analysis by LC-MS/NIS demonstrated that the CPT-PP contains 5% of PA, 2% of LOG, each 1.5% of AOG, EOG, SOG and EO, and 0.5% of POG.

Comparative Example 1

Preparation of Collagen Peptide Mixture not Containing Specific Peptide

A collagen peptide mixture (CPT-JB) for comparison containing no specific peptide other than GPO, for use in the later-described performance evaluation tests and formulation examples, was obtained in the following manner.

To be more specific, 1 kg of gelatin (type I collagen) which is a thermal-denatured product of collagen derived from pig skin was dissolved in 4 L of 20 mM Tris-HCl buffer (pH 7.5) under warming, and cooled to 40° C., and then as a primary enzymatic reaction, 1 g of collagenase (manufactured by NITTA GELATIN INC., Collagenase N2) was added, and the reaction was retained at pH 7.0 to 7.8, at 40° C. for 18 hours, to conduct an enzymatic degradation treatment. Then the solution obtained by the enzymatic hydrolysis treatment was heated at 100° C. for 10 minutes, and then cooled to 60° C., and filtered by using activated charcoal and a filtration aid (diatomaceous earth), and the obtained mother liquor was subjected to a high temperature sterilization treatment at 120° C. for 3 seconds. Then, the mother liquor after sterilization was spray-dried, to obtain CPT-JB.

The CPT-JB was analyzed by TLC in a similar manner to the case of the CPT-PU, and further subjected to a LC-MS/MS analysis, and no other specific peptide than GPO was observed.

Comparative Example 2

Preparation of Collagen Peptide Mixture not Containing Specific Peptide

A collagen peptide mixture (CPT-Cont) for comparison containing no specific peptide, for use in the later-described performance evaluation tests and formulation examples, was obtained in the following manner.

To be more specific, 10 g of collagen peptide HACP-01 (manufactured by JELLICE Co., Ltd., collagenase degradation product) and 0.1 g of protease N "AMANO" G (manufactured by Amano Enzyme Inc., derived from *Bacillus subtilis*) were dissolved in water, and heated at 55° C. for 1 hour to conduct an enzymatic treatment, and then heated at 80° C. for 30 minutes to inactivate the enzyme. This enzyme-treated solution was lyophilized to obtain CPT-Cont.

The CPT-Cont was analyzed by TLC in a similar manner to the case of the CPT-PU, and further subjected to a LC-MS/MS analysis, and no specific peptide was observed.

[Performance Evaluation Tests]

The details of performance evaluation tests conducted by using each of the peptides and collagen peptide mixtures as described above will be shown below.

<Evaluation Test 1: DPPIV Inhibitory Activity>

DPPIV inhibitory activity was determined by using a DPPIV inhibitory activity measuring kit "DPPIV Drug Discovery Kit-AK-499" (manufactured by BIOMOL). As a peptide sample substrate, H-Gly-Pro-7-amino-4-methylcoumarin "P189-9090 AMC substrate" (manufactured by BIOMOL) was used, and as an enzyme, DPPIV "E434-9090 DPPIV enzyme; human recombinant" (manufactured by BIOMOL) was used.

Inhibitory activity was evaluated by the concentration at which 50% of DPPIV activity was inhibited. The one showing a lower value has higher inhibitory activity, and efficiently inhibits the DPPIV activity with a small amount.

Results for peptides are shown in Table 1, and results for collagen peptide mixtures are shown in Table 2.

TABLE 1

| Peptide | Specific peptide | | | | | | |
|---|---|---|---|---|---|---|---|
| | PA | LO | EO | IO | SO | LOG | POG |
| IC$_{50}$ (mM) | 1.0 | 1.7 | 1.5 | 2.9 | 3.6 | 0.28 | 0.6 |

| Peptide | Specific peptide | | | | | Other | |
|---|---|---|---|---|---|---|---|
| | EOG | SOG | AOG | AO | GPO | (POG)$_5$ | PAG |
| IC$_{50}$ (mM) | 2.9 | 3.0 | 6.0 | >10 | >10 | >10 | >10 |

TABLE 2

| Collagen peptide mixture | Containing specific peptide | | | | | | Not containing | |
|---|---|---|---|---|---|---|---|---|
| | CPT-PU | CPT-P-H | CPT-P-20 | CPT-P-22 | CPT-P-25 | CPT-PP | CPT-JB | CPT-Cont |
| IC$_{50}$ (mg/mL) | 0.62 | 0.65 | 0.61 | 0.75 | 0.82 | 0.27 | >5 | 4.22 |

<Evaluation Test 2: GLP-1 Secretion Accelerating Activity>

Human-derived intestinal tract L cells (NCI-H716 cell: manufactured by ATCC) were inoculated at 5×10$^5$ cells/mL× 200 μL (1×10$^5$ cells/well) in a RPIM medium containing 10% FBS (manufactured by ATCC) on a Pre-coated poly-L-lysin plate (96 wells plate) and cultured for 2 days. After confirming that the cells were adhered to the plate, the medium was replaced by a test medium (146 mM NaCl, 5 mM KCl, 1.5 mM CaCl$_2$, 1 mM MgSO$_4$, 20 mM HEPES, 5.6 mM glucose, 2 mg/mL BSA) and a sample was added at a final concentration of 5 mM. A culture supernatant after 1 hour was 30-fold diluted with PBS, and tested with GLP-1 ELISA kit (manufactured by Levis) according to the protocol.

Based on GLP-1 secretion in the case not added with the sample (Blank) as 100%, a GLP-1 secretion accelerating percentage in the fraction added with 5 mM sample was calculated.

Results for peptides are shown in Table 3, and results for collagen peptide mixtures are shown in Table 4.

TABLE 3

| Peptide | | GLP-1 secretion accelerating percentage (%) |
|---|---|---|
| Specific peptide | Blank | 100 ± 10.5 |
| | LOG | 326 ± 17 |
| | GPO | 278 ± 60 |
| | (POG)$_5$ | 271 ± 96 |
| | PO | 154 ± 44 |
| | OG | 152 ± 22 |
| | EOG | 307 ± 84 |
| | SO | 161 ± 37 |
| | PG | 168 ± 15 |
| | PA | 133 ± 85 |
| | PP | 167 ± 53 |
| | EO | 148 ± 66 |
| | AOG | 120 ± 5 |
| | AO | 262 ± 71 |

(n = 4) GLP-1 concentration of Blank was 742 ± 231 pg/mL

TABLE 4

| Collagen peptide mixture | | GLP-1 secretion accelerating percentage (%) |
|---|---|---|
| Containing specific peptide | Blank | 100 ± 10.5 |
| | CPT-PU | 600 ± 20 |
| | CPT-P-H | 755 ± 150 |
| | CPT-P-20 | 355 ± 37 |
| | CPT-P-22 | 344 ± 30 |
| | CPT-P-25 | 141 ± 28 |
| | CPT-PP | 553 ± 25 |
| Not containing | CPT-JB | 110 ± 26 |

(n = 4) GLP-1 concentration of Blank was 742 ± 231 pg/mL

<Evaluation Test 3: Intestinal Tract Absorptivity>

Male Wistar rats (170 g) were fasted overnight before subjected to the experiment. As a test sample, 215 nmol/10 mL of each of the peptides was used, and intragastrically administered.

As a test method, heart and portal vein of each rat were attached with a cannula to make one-directional perfusion. As a perfusate, a Krebs-Ringer bicarbonic acid liquid (KRB liquid, pH 7.4) composed of 9.0 g of NaCl, 8 mL of 5.75% KCl, 2 mL of 10.55% KH$_2$PO$_4$, 2 mL of 19% MgSO$_4$, 2.73 g of NaHCO$_3$, 3.43 g of glucose, and 1255 mL of water, and to which were added 10 g of bovine serum albumin, 0.5 mL of dexamethasone (0.123 mg/mL) and 0.5 mL of noradrenaline (0.024 mg/mL) per 500 mL of the KRB liquid was used.

To a perfusion sample solution (5.0 mL) collected from the portal vein was added 0.5 mL of 30% sulfosalicylic acid and stirred vigorously, and left overnight in a refrigerator. This sample was centrifuged at 3000 rpm for 10 minutes, to remove protein. For the supernatant of centrifugation, an amount of hydroxyproline in 0.5 mL was colorimetrically quantified, and an amount of free-type Hyp was obtained.

Further, 3.0 mL of the supernatant of centrifugation was weighed into a screw-top test tube, and thereto an equivalent amount of concentrated hydrochloric acid was added, and hydrolyzed at 110° C. for 24 hours. After concentrating and drying the resultant in an evaporator, and removing the hydrochloric acid, the solid was dissolved in 5 mL of distilled water, and several drops of a saturated lithium hydroxide solution was added thereto to adjust pH at 5 to 7, and the volume was fixed at 10 mL. For 2 mL of this solution, an amount of hydroxyproline was colorimetrically quantified to obtain a total Hyp amount. The value obtained by subtracting the amount of free-type Hyp before hydrolysis from the total Hyp amount after hydrolysis is an amount of peptide-form Hyp. From this amount of peptide-form Hyp, a quantitative value of absorption of each peptide into rat portal vein perfusate in the test sample was first determined.

The colorimetric quantification of the amount of hydroxyproline was conducted by a Firschein and Shill method, and was concretely conducted in the following manner.

That is, 2 mL of 2-propanol was added to 2 mL of a sample solution and stirred thoroughly. Then, 0.5 mL of a chloramine T liquid being an oxidizing agent was added to the mixture, and left still for accurately 4 minutes, and then cooled on ice. Then, 5 mL of a p-dimethylaminobenzaldehyde solution was added to the mixture and stirred thoroughly, and then heated in a boiling water bath for accurately 2 minutes. Then, the reaction was immediately cooled on ice, and left still for 1 hour, and then colorimetrically quantified at a wavelength of 575 nm.

As the chloramine T liquid, a solution prepared by dissolving chloramine T (5 g) in 50 mL of distilled water was stored in a refrigerator, and a liquid prepared by diluting the solution with acetic acid buffer (pH 6.0) at a ratio of 1:4 directly before use was used. Further, the p-dimethylaminobenzaldehyde solution (Erich solution) was prepared by dissolving 20 g of p-dimethylaminobenzaldehyde powder in 22 mL of concentrated hydrochloric acid under heating in boiling water, and immediately cooling the same in ice water, and adding 122 mL of 2-propanol and dissolving it under stirring.

Next, peptides collected in the rat portal vein perfusate, namely the aforementioned intestinally absorbed peptides were identified and quantified by the following HPLC analysis and mass spectrometry (LC/MS/MS).

(HPLC Analysis)

Analysis of the peptide in the perfusate was conducted by reverse-phase HPLC analysis. As a HPLC device, an LCSS-905 system manufactured by JASCO Corporation, consisting of a liquid feeding pump, a degasser, an automatic sampler, a column open, a UV spectrophotometer, a printer, and a system controller was used. As a reverse-phase column, Nova Pak C18 (3.9×150 mm) was used.

A linear gradient mobile phase of a 0.1% TFA-containing acetonitrile-water system was used, and the injection amount of the sample was 70 pt and the flow rate was 1 mL/min.

(LC/MS/MS Analysis)

As a HPLC device, U980HPLC (manufactured by JASCO Corporation) attached with an ODS(C18) column (Mightysil RP-18, 2×250 mm, manufactured by Kanto Chemical Co., Ltd.) was used. As a mobile phase solvent, a 0.2% formic acid-containing acetonitrile-water system was used, and the concentration of acetonitrile was increased from 0% to 40% over 40 minutes by a linear gradient, and it was washed with 100% acetonitrile for 10 minutes. The sample injection amount was 10 µL, and the column temperature was 40° C.

MS analysis was conducted by a MS/MS system using a Quattro LC mass spectrophotometer (Micromass, Manchester, UK) according to a four-channel Multiple Reaction Monitoring method. To be more specific, the elute from HPLC was monitored by m/z being $[M+H]^+$ and by m/z of its fragment ion species. At this time, $[M+H]^+$ m/z was monitored using 302.2>189.4 for LOG; 286.1>189.3 for POG; 187.1>70.3 for PA; 261.1>243.4 for EO, 245.1>132.3 for LO; 245.2>132.1 for IO; 318.1>225.4 for EOG; 276.1>189.4 for SOG; 219.1>132.2 for SO; and 260.1>189.4 for AOG.

The perfusate was treated with sulfosalicylic acid in a final concentration of 3%, to remove protein. The supernatant liquid was lyophilized and 10 mg of a dry powder was dissolved in distilled water, and subjected to a positive ion exchange resin column to obtain an ammonia elution fraction. After removing the solvent, the fraction was dissolved in distilled water and subjected to LC/MS/MS analysis.

The result is shown in Table 5.

TABLE 5

| Peptide | | Amount of peptide identified after absorption (nmol/mL) |
|---|---|---|
| Specific peptide | PA | 152.6 ± 1.1 |
| | LO | 167.7 ± 0.9 |
| | EO | 156.0 ± 1.3 |
| | IO | 163.4 ± 1.9 |
| | SO | 116.1 ± 0.9 |
| | LOG | 116.1 ± 1.0 |
| | POG | 129.0 ± 1.0 |
| | EOG | 110.0 ± 0.9 |
| | SOG | 103.2 ± 1.0 |
| | AOG | 66.7 ± 1.3 |
| | AO | 71.0 ± 0.9 |
| | (POG)$_5$ | 10.8 ± 0.9 |
| | GPO | 2.2 ± 0.0 |
| Other | PAG | 105.4 ± 1.3 |

<Evaluation Test 4: Evaluation of Sugar Tolerance by Glucose Loading Test>

Six-weeks old male ob/ob mice (Japan SLC) were allowed to acclimate by feeding with normal diet (MF, Oriental Yeast) for 7 days, and subjected to the experiment. After fasting the same mice overnight (16 hours), each collagen peptide (0.85 g/kg) or casein (0.85 g/kg, manufactured by DMV, Netherlands) was orally administered, and glucose (2 g/kg) was orally administered after 30 minutes, and the effect on the sugar tolerance was examined by a glucose loading test (2 g/kg). After 0, 15, 30, 60 and 120 minutes, the blood sugar level was measured by using a blood glucose measuring apparatus (Glutest ace R, SANWA KAGAKU KENKYUSHO CO., LTD.), and $AUC_{0-120\ min}$ was calculated, and evaluated.

The results are as shown in Table 6.

TABLE 6

| Collagen peptide mixture | | $AUC_{0-120\ min} \times 1000$ (min mg/dL) |
|---|---|---|
| Containing specific peptide | Casein | 40.0 ± 2.0 |
| | CPT-PU | 29.0 ± 1.0* |
| | CPT-P-H | 26.3 ± 1.5* |
| | CPT-P-20 | 25.0 ± 1.3* |
| | CPT-P-22 | 28.2 ± 1.1* |
| | CPT-P-25 | 27.5 ± 1.8* |
| | CPT-PP | 25.4 ± 2.1* |
| Not containing | CPT-JB | 38.7 ± 2.4 |

*There is significant difference in comparison with casein (P < 0.05).

<Discussion of Results of Performance Evaluation Tests>

As described above, Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp, Ser-Hyp-Gly, Gly-Pro-Hyp, (Pro-Hyp-Gly)$_5$, Pro-Hyp, Hyp-Gly, Pro-Gly, Pro-Pro and Ala-Hyp have DPPIV inhibitory activity. In particular, Glu-Hyp-Gly, Glu-Hyp, Leu-Hyp-Gly, Pro-Ala, Ser-Hyp, Ala-Hyp-Gly, Pro-Hyp-Gly, Leu-Hyp, Ile-Hyp and Ser-Hyp-Gly have high DPPIV inhibitory activity. Glu-Hyp-Gly, Glu-Hyp, Leu-Hyp-Gly, Pro-Ala, Ser-Hyp, Ala-Hyp-Gly, Gly-Pro-Hyp, (Pro-Hyp-Gly)$_5$, Pro-Hyp, Hyp-Gly, Pro-Gly, Pro-Pro and Ala-Hyp have GLP-1 secretion accelerating activity. Further, these peptides are little degraded into amino acids because of high tolerance to digestive enzymes, and are rapidly absorbed into blood from the intestinal tract, or directly absorbed into an intestinal tract surface cell or a L cell from the intestinal tract, so that they exhibit an excellent effect when they are orally administered.

Formulation Examples

Using the specific peptides, preparations of the present invention were obtained. The formulation examples are shown below.

Examples 7 to 12

The ingredients in the blending shown in Table 7 were mixed, and crystalline cellulose as an excipient was used in a proportion of 10 parts with respect to the entirety of the blending described in Table 7, and formed into a tablet according to a routine method, to obtain the preparations according to Examples 7 to 12 that can be used for oral administration.

TABLE 7

| | Example 7 (wt. %) | Example 8 (wt. %) | Example 9 (wt. %) | Example 10 (wt. %) | Example 11 (wt. %) | Example 12 (wt. %) |
|---|---|---|---|---|---|---|
| LOG | 2 | — | — | — | — | — |
| CPT-P-20 | — | 76 | — | — | — | — |
| CPT-PU | — | — | 76 | — | — | — |
| CPT-P-H | — | — | — | 76 | — | — |
| CPT-P-22 | — | — | — | — | 76 | — |
| CPT-P-25 | — | — | — | — | — | 76 |
| CPT-JB | 74 | — | — | — | — | — |
| Calcium (burnt and ground oyster shell) | 6 | 6 | 6 | 6 | 6 | 6 |
| Glucosamine hydrochloride | 14 | 14 | 14 | 14 | 14 | 14 |
| Vitamin C | 4 | 4 | 4 | 4 | 4 | 4 |

Example 13

A chewable type tablet was produced by using the CPT-PU.

Concretely, the following blending ingredients were mixed, and chewable type tablets of 0.8 g per tablet were prepared by using a tablet compressor. This chewable type tablet contained 1% of POG, 2% of PA, 1% of AOG, and each 0.75% of LOG, EOG and SOG in the total of 100%.

| CPT-PU | 50.0 kg |
|---|---|
| Ascorbic acid | 10.0 kg |
| MICROCALMAG S (produced by SK Foods Co., Ltd.) | 4.6 kg |
| Mabit (produced by Hayashibara Co., Ltd.) | 19.0 kg |
| Crystalline cellulose | 10.0 kg |
| Emulsifying agent | 3.2 kg |
| Aspartame | 0.5 kg |
| Fermented milk powder | 1.4 kg |
| Powder flavor | 1.0 kg |
| Citric acid | 0.3 kg |

Example 14

Using the above CPT-PU, powder consomme soup (6.0 g per package) to be dissolved in 100 to 140 mL of hot water before eaten was prepared by mixing the following blending ingredients. This powder consomme soup contained 0.7% of POG, 1.4% of PA, 0.7% of AOG, and each 0.6% of LOG, EOG and SOG in the total of 100%.

| CPT-PU | 35.0 kg |
|---|---|
| Chicken extract powder | 25.0 kg |
| Sodium chloride | 18.0 kg |
| Glucose | 7.7 kg |
| Calcium lactate | 7.0 kg |
| Sodium glutamate | 4.0 kg |
| Onion extract powder | 1.0 kg |
| HVP | 1.0 kg |
| Beef flavor | 0.5 kg |
| Disodium 5'-ribonucleotide | 0.5 kg |
| White pepper | 0.2 kg |
| Turmeric | 0.1 kg |

Example 15

Using the above CPT-PU, powder juice (13.0 g per package) to be dissolved in 100 to 150 mL of water before drinking was prepared by mixing the following blending ingredients. This powder juice contained 0.8% of POG, 1.6% of PA, 0.8% of AOG, and each 0.6% of LOG, EOG and SOG in the total of 100%.

| CPT-PU | 40.4 kg |
|---|---|
| Sodium ascorbate | 1.2 kg |
| Erythritol | 52.0 kg |
| Acesulfame K | 0.1 kg |
| Aspartame | 0.1 kg |
| Sodium citrate | 0.8 kg |
| Citric acid (crystal) | 4.6 kg |
| Muscat flavor | 0.8 kg |

Example 16

Using the above CPT-PU, other blending ingredients were dissolved in purified water according to the following blending ingredients, and the solution was adjusted to pH 3.5, B'×9.0%, and then subjected to a heat sterilization treatment at 110° C. for 30 seconds, and cooled to 10° C. and aseptically packed in a paper package, to prepare a soft drink (125 mL per package). This soft drink contained 0.05% of POG, 0.1% of PA, 0.05% of AOG, and each 0.04% of LOG, EOG and SOG in the total of 100%.

| CPT-PU | 2.5 kg |
|---|---|
| Vitamin mix DN (produced by BASF Japan) | 0.1 kg |
| Erythritol | 5.5 kg |
| Acesulfame K | 0.015 kg |
| Aspartame | 0.005 kg |
| Citric acid | about 0.6 kg |
| Fruit mix flavor | 0.16 L |
| Lychee flavor | 0.04 L |
| Purified water | balance (for making up for the total of 100.0 kg) |

Example 17

First, of the following blending ingredients, the CPT-PU and gelatin were immersed in purified water (B) and allowed to swell for 30 minutes, and then they were completely dissolved by heating to 80° C. for 30 minutes, to prepare a gelatin solution. Then, of the following blending ingredients, milk oligosaccharide, powder malt reducing sugar, erythritol, and indigestible dextrin were dissolved in purified water (A), and boiled down, and then thereto was added Aspartame, the aforementioned gelatin solution, citric acid (crystal) dissolved in advance in part of purified water (A), peppermint flavor, mint flavor, lemon flavor and a safflower yellow pigment, and prepared into B'×79 to 81%, and then defoamed, and packed in a starch mold and dried at room temperature for 24 hours, to prepare gummy jelly (4 g per piece). This gummy jelly contained 0.1% of POG, 0.2% of PA, 0.1% of AOG, and each 0.08% of LOG, EOG and SOG in the total of 100%.

| CPT-PU | 5.0 kg |
|---|---|
| Milk oligosaccharide | 41.0 kg |
| Powder malt reducing sugar | 31.0 kg |
| Erythritol | 5.0 kg |
| Indigestible dextrin | 5.0 kg |
| Aspartame | 0.05 kg |
| Gelatin (APH250, produced by Nitta Gelatin) | 7.0 kg |
| Citric acid (crystal) | 1.2 kg |
| Peppermint flavor | 0.6 L |
| Mint flavor | 0.2 L |
| Lemon flavor | 0.7 L |

-continued

| | |
|---|---|
| Safflower yellow pigment | appropriate amount |
| Purified water (A) | 20.0 L |
| Purified water (B) | 18.0 L |

Example 18

By solubilizing in sterilized saline so that LOG was 2.5 mM using the preparation of Example 6, a liquid preparation for injection into vein was obtained.

INDUSTRIAL APPLICABILITY

The present invention provides a therapeutic or preventive agent for diabetes. The present invention also provides a collagen peptide mixture that can be used as a therapeutic or preventive agent for diabetes, and a method for producing the same.

The invention claimed is:

1. A method for treatment of diabetes comprising administering the dipeptide Pro-Ala or a pharmaceutically acceptable salt thereof to a subject in need thereof.

2. A method for inhibiting dipeptidyl peptidase IV or accelerating glucagon-like peptide-1 secretion, comprising administering the dipeptide Pro-Ala or a pharmaceutically acceptable salt thereof to a subject in need thereof.

3. The method of claim 1, further comprising administering at least one dipeptide or tripeptide selected from the group consisting of Glu-Hyp-Gly, Glu-Hyp, Leu-Hyp-Gly, Ser-Hyp and Ala-Hyp-Gly, and pharmaceutically acceptable salts thereof.

4. The method of claim 2, further comprising administering at least one dipeptide or tripeptide selected from the group consisting of Glu-Hyp-Gly, Glu-Hyp, Leu-Hyp-Gly, Ser-Hyp and Ala-Hyp-Gly, and pharmaceutically acceptable salts thereof.

5. A method for treatment of diabetes comprising administering two or more dipeptides or tripeptides selected from the group consisting of Glu-Hyp-Gly, Glu-Hyp, Leu-Hyp-Gly, Pro-Ala, Ser-Hyp, Ala-Hyp-Gly, and pharmaceutically acceptable salts thereof to a subject in need thereof.

6. The method of claim 1, wherein the dipeptide Pro-Ala or the pharmaceutically acceptable salt thereof is administered orally or parenterally as a pharmaceutical preparation with a pharmaceutically acceptable carrier.

7. The method of claim 6, wherein the dipeptide Pro-Ala or the pharmaceutically acceptable salt thereof is present in the oral pharmaceutical preparation in a proportion of 0.001 parts by weight or more of the oral pharmaceutical preparation or in the parenteral pharmaceutical preparation in an amount of 0.1 mol/L or more in the parenteral pharmaceutical preparation.

8. The method of claim 2, wherein the dipeptide Pro-Ala or pharmaceutically acceptable salt thereof is administered orally or parenterally as a pharmaceutical preparation with a pharmaceutically acceptable carrier.

9. The method of claim 3, wherein the dipeptides or tripeptides or pharmaceutically acceptable salts thereof are administered orally or parenterally as a pharmaceutical preparation with a pharmaceutically acceptable carrier.

10. The method of claim 9, wherein the amount of dipeptides and tripeptides administered orally is about 0.1 to 1000 mg and parenterally is about 0.1 to 100 mg.

11. The method of claim 4, wherein the dipeptides or tripeptides or pharmaceutically acceptable salts thereof are administered orally or parenterally as a pharmaceutical preparation with a pharmaceutically acceptable carrier.

12. The method of claim 5, wherein the dipeptides or tripeptides or pharmaceutically acceptable salts thereof are administered orally or parenterally as a pharmaceutical preparation with a pharmaceutically acceptable carrier.

13. The method of claim 3, wherein the dipeptides and tripeptides administered are prepared by subjecting collagen or gelatin to a two-step enzymatic treatment, wherein an enzyme used in a primary enzymatic treatment is selected from the group consisting of collagenase, thiol protease, serine protease, acidic protease, alkaline protease and metal protease, and an enzyme used in a secondary enzymatic treatment is an enzyme having aminopeptidase N activity, or an enzyme having both aminopeptidase N activity and prolyl tripeptidyl aminopeptidase activity, or a combination of an enzyme having aminopeptidase N activity and an enzyme having prolyl tripeptidyl aminopeptidase activity.

14. The method of claim 5, wherein the three or more dipeptides or tripeptides and pharmaceutically acceptable salts are contained in a collagen peptide mixture, and wherein the three or more dipeptides or tripeptides and pharmaceutically acceptable salts thereof are 2% by weight or more of the collagen peptide mixture.

15. The method of claim 3, wherein a preparation containing dipeptides and tripeptides is administered to a subject in need thereof, wherein the dipeptides and tripeptides consist of Pro-Ala and one or more dipeptides or tripeptides selected from the group consisting of Glu-Hyp-Gly, Glu-Hyp, Leu-Hyp-Gly, Pro-Ala, Ser-Hyp, Ala-Hyp-Gly, and pharmaceutically acceptable salts thereof.

* * * * *